(12) United States Patent
Brommersma et al.

(10) Patent No.: US 6,471,701 B2
(45) Date of Patent: Oct. 29, 2002

(54) HIGH-FREQUENCY RESECTOSCOPE IMPLEMENT

(75) Inventors: Pieter Brommersma, Bargteheide (DE); Yasuhiko Kikuchi, Sagamihara Kanagawa (JP)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

(21) Appl. No.: 09/881,504

(22) Filed: Jun. 14, 2001

(65) Prior Publication Data

US 2001/0053908 A1 Dec. 20, 2001

(30) Foreign Application Priority Data

Jun. 16, 2000 (DE) .......................................... 100 28 850

(51) Int. Cl.⁷ .............................................. A61B 18/18

(52) U.S. Cl. .......................................... 606/46; 606/48

(58) Field of Search ................................ 606/41, 45–48

(56) References Cited

U.S. PATENT DOCUMENTS

| 4,116,198 | A | * | 9/1978 | Roos ............................. 606/46 |
| 5,196,011 | A | * | 3/1993 | Korth et al. ................... 606/46 |
| 5,919,189 | A | * | 7/1999 | Benderev ....................... 606/45 |
| 5,919,191 | A | * | 7/1999 | Lennox et al. ................. 606/48 |
| 5,993,445 | A | * | 11/1999 | Issa .............................. 606/46 |

* cited by examiner

Primary Examiner—Michael Peffley
(74) Attorney, Agent, or Firm—Rankin, Hill, Porter & Clark LLP

(57) ABSTRACT

An hf resectoscope implement for cutting body tissue in a body cavity filled with an electrically conducting fluid and comprising a loop support and a loop-shaped cutting electrode mounted distally on the support. A plane of the cutting electrode slants relative to a longitudinal axis of the loop support. The implement also includes a neutral electrode mounted on the support. An insulator is mounted at the loop support between the electrodes such that any straight geometric line between the electrodes passes through the insulator. The neutral electrode and the insulator are configured to not significantly hamper the view available via optics fitted in the resectoscope stem tube.

12 Claims, 6 Drawing Sheets

HIGH-FREQUENCY RESECTOSCOPE IMPLEMENT

BACKGROUND OF THE INVENTION

1. Filed of the Invention

The present invention generally relates to a high-frequency (hf) resectoscope implement to cut body tissue in a body cavity filled with an electrically conducting fluid, such as the human bladder. More particularly, the present invention is directed toward an hf resectoscope implement having a loop support and a loop-shaped cutting electrode mounted distally to the loop support, wherein a plane of the electrode slants relative to a longitudinal axis of the loop support.

2. Description of Related Art

Conventional resectoscopes make use of the mono-pole technique, wherein an hf current is set up between the resection electrode, which is the active electrode, through the body of the patient and a neutral electrode of substantial surface, which is mounted externally on the patient, for instance on the thigh.

However, passing current through the patient's body entails certain risks which, even when the resectoscope is expertly handled, can never be completely eliminated. For instance, uncontrolled or stray leakage currents may lead to painful skin burns on the patient when the patient contacts a metallic object such as the operating table. If there are current-induced muscle contractions, there is danger that the patient will move in an uncontrolled and sudden manner and, thus, be subjected to unintended cutting injury by the resectoscope implement. Latently, there is also a danger that the muscles or nerves near the resection area may be damaged, at least temporarily, by stray currents.

The above dangers can be widely eliminated using bi-polar techniques wherein both the active electrode and the neutral electrode are inserted into the patient's body. As a result, the hf current is set up only between the two implement electrodes, but not, and if so only over defined short paths, through the body of the patient.

A bi-polar hf resectoscope implement is disclosed in the German Offenlegungsschrift 25 21 719, which is considered the nearest state of the art. Therein, the neutral electrode is mounted at the loop support arm and together with the loop support arm can be axially moved into and out of the stem of a resectoscope. This feature offers the advantage that the spacing between the active and neutral electrodes remains constant and that, accordingly, the current paths are also substantially constant. Therefore, the cutting action of the cutting electrode is approximately constant at any advanced position of the implement.

As regards implements of this kind, the neutral electrode is in the fluid and spaced from the body tissue. When the active electrode makes contact with the tissue, the hf current passes through the body tissue and then into the fluid and from the fluid back to the neutral electrode.

However, the bi-polar technique incurs problems of current losses arising from current passing directly through the electrically well-conducting fluid between the active and the neutral electrodes without passing through the body tissue. Consequently, only a portion of the current applied to the hf implement will effect the cutting by the active electrode, namely that portion which passes from the active electrode into the body tissue and from there back to the neutral electrode.

These current losses are amplified especially if the intervention takes place in body cavities containing an especially electrically well-conducting fluid. This may occur, for instance, when resection rinsing is carried out using a fluid rich in electrolyte, illustratively an isotonic fluid. In such cases even the major portion of the current goes straight from the cutting site, that is, from the active electrode to the neutral one, without contributing to cutting. Accordingly, cutting by means of hf resectoscope implements of the state of the art in body cavities filled with an electrically conducting fluid is impossible, or only possible in an unsatisfactory manner.

The state of the art meets this problem by typically using electrically poorly conducting fluids when rinsing. It must be considered, however, that blood vessels are opened during resection and that part of the fluid inevitably enters the blood circulation of the patient. As a result, the patient may experience a complex of symptoms, also known as the TUR [transurethral resection] syndrome, such as vomiting, heart arrhythmia, kidney failure, shock. Therefore, using electrically poorly conducting fluids as rinses appears inappropriate, especially when it is realized that the above-noted reactions arise less intensely, sometimes not at all, when the isotonic fluids are used.

SUMMARY OF THE INVENTION

Therefore, an objective of the present invention is to create an hf resectoscope implement that overcomes the above difficulties and is optimized for the resection of body tissue in a body cavity filled with an electrically well-conducting fluid.

The effectiveness and, hence, an advantage of the present invention is an insulator structure, hereafter "insulator", between the cutting electrode and the neutral one, that hampers the straight current between the two electrodes. Hence, the present invention reduces current flow directly between the electrodes, so that a larger portion of the supplied hf power is fed from the cutting electrode into the body tissue and there into cutting work. Vice-versa, less power is required by the implement of the invention relative to those of the state of the art to attain the cutting.

The basic idea of mounting an insulator between the active and the neutral electrode is known from the extra-species patent document WO 97/24993 which, in its FIG. 9, shows an implement comprising a rolling, spherical electrode of vaporization mounted in rotatable manner on a support. The ball's axis of rotation is perpendicular to the support's longitudinal axis. A hemispheric insulator, which also rests on the support, is mounted a slight distance above the ball. The neutral electrode is mounted on the insulator side, which is away from the vaporization electrode. In this manner a lesser straight current is attained between the active electrode and the neutral one. However, this design masks much of the field of view otherwise available to the surgeon. This drawback is inherent when using a spherical electrode.

The neutral electrode of the bipolar hf implement may, in principle, be mounted anywhere on the loop support. In further accordance with the present invention, however, the neutral electrode is configured distally at the loop support. This feature offers the advantage that when the implement is inserted into the stem tube of the resectoscope it need not move past the observation or illumination optics mounted in the stem tube. Instead, if the implement is properly dimensioned, the implement will be distally in front of the optics when it is inserted. In order to prevent arcing, care must be taken that the neutral electrode does not touch the optics. It is understood that the insulator must also be mounted distally at the loop support so that it can shield the electrodes from each other.

The cutting electrode, the insulator and the neutral electrode all are mounted on the loop support and held in place by the loop support. In the most general design, the three elements may be mounted in a mutually independent manner on the loop support, for instance by means of arms spreading from the loop support. Such a feature, however, is both uneconomical as regards manufacture and of low mechanical strength. Therefore, in accordance with another feature of the present invention, the neutral electrode is mounted directly on the insulator side away from the cutting electrode. Accordingly, the insulator supports the neutral electrode and imparts mechanical strength to the neutral electrode while improving the shielding geometry.

The geometry of the neutral electrode is widely arbitrary. However, in accordance with another feature of the invention, the-neutral electrode is mounted face-to-face or surface-on-surface to the insulator to be better held in place. Moreover, the topological design of the neutral electrode offers the advantage that current from the cutting electrode into the tissue and from there back to the neutral electrode is spread out over a large area and, hence, can enter the neutral electrode at low current density. This feature also means that, in the event of accidental contact of the topological neutral electrode with the body tissue, the consequence shall be only slight on this tissue. Additionally, the shielding geometry is improved.

The mechanical strength of the neutral electrode affixation and the shielding geometry may be improved further in that, according to another aspect of the invention, the neutral electrode is, to some extent, embedded in the insulator. This feature, furthermore, assures that the neutral electrode cannot make contact with the stem or the optics during retraction into the resectoscope.

However, a problem arises if the neutral electrode is fully inserted into the insulator. Namely, when the active electrode reaches the resectoscope's cutting edge, the neutral electrode, on one hand, is masked by the insulator and, on the other hand, is masked by the distal end zone of the resectoscope stem, which usually is insulating. Consequently, the current is interrupted and, with it, the cutting action before the cutoff strip of tissue has been separated at the cutting edge.

In further accordance with the present invention, this difficulty is averted in a simple and advantageous manner by the neutral electrode comprising a distal zone which is not masked by the insulator. This zone is left uncovered also by the cutting electrode in the inserted state (i.e., when reaching the cutting edge of the resectoscope) and, hence, it is freely accessible to the return current. Thus, the current is uninterrupted, and the strip of body tissue can be separated at the cutting edge.

The insulator may be a flat plate. However, according to another feature of the invention, the insulator has a curvature that is advantageously inverted relative to that of the cutting electrode. This curvature improves the surgeon's view through the insulator and the cutting electrode. Also, the inserted electrode is more easily guided over the resectoscope optics, especially when the optics is configured eccentrically above the resectoscope center axis.

The loop support holding the cutting electrode may be a single arm. In this case the electrodes are termed single bar electrodes. Typically, however, the loop support at the distal end is bifurcated to form two parallel bars. The cutting electrode, also referred to as the cutting loop, is substantially semi-circular and held in place between the two bars at a slant to the loop support's longitudinal axis. As a rule, the plane of the loop is approximately perpendicular to the loop support's longitudinal axis. However, the invention is not restricted to such a constraint and also includes slant angles other than 90°.

As regards the bifurcated loop supports, the present invention advantageously proposes distally adjoining the insulator to both bars. In this manner the insulator assures good mechanical strength of the distal zones of the hf resectoscope implement. Preferably, the insulator curvature is inverted relative to that of the cutting electrode resting on the bars of bifurcated loop supports. In this manner a free central zone remains between the cutting electrode and the insulator to allow unhampered viewing by the surgeon of the field of surgery.

In accordance with further features of the present invention, the axial projection of the cutting electrode together with that of the curved insulator bearing the neutral electrode essentially subtend or define a circle. It is understood that the circle diameter must be slightly less than the inside diameter of the resectoscope's stem tube. Again, it is understood that in resectoscopes in which the stem tube exhibits an oval cross-section, the above axial projection will also be oval. These advantages are those already cited in the preceding paragraph, in particular as regards the surgery field of view.

In further accordance with the present invention, the insulator is integral and consists of a segment, a curvature of which is inverted relative to that of the cutting electrode, and a segment, which is shaped like the cutting electrode and mounted distally from it. Therefore, the insulator, per se, already substantially subtends a ring or circle. This feature, in conjunction with affixing the cutting electrode to the insulator segment and closely adjoining the insulator segment, contributes to high mechanical strength. The service life of the electrodes of the invention is very long because the cutting loop zone, which is especially stressed when the hf implement is working, is mechanically reinforced by the lower insulator segment. Additional advantages relate to implement installation and advantageous shielding by the insulator of the cutting loop.

In further accordance with the present invention, the cutting electrode at its lower zone assumes the shape of a wire flattened into a lamella. The lamella is mounted on the outside of the insulator segment which closely adjoins the cutting electrode. This mechanically-strong configuration allows coagulating by means of the lower side of the lamellar strip while the top side is shielded by the insulator. Accordingly, the insulator of the invention shields those parts of the cutting electrode which are not, nor should be, in contact with the tissue and, furthermore, reduces substantially further the current straight between the cutting and neutral electrodes.

BRIEF DESCRIPTION OF THE DRAWINGS

Further details and features of the invention are elucidated in the following schematic drawings.

DETAILED DESCRIPTION OF THE PREFERRED EMBODIMENTS

Figure 1:
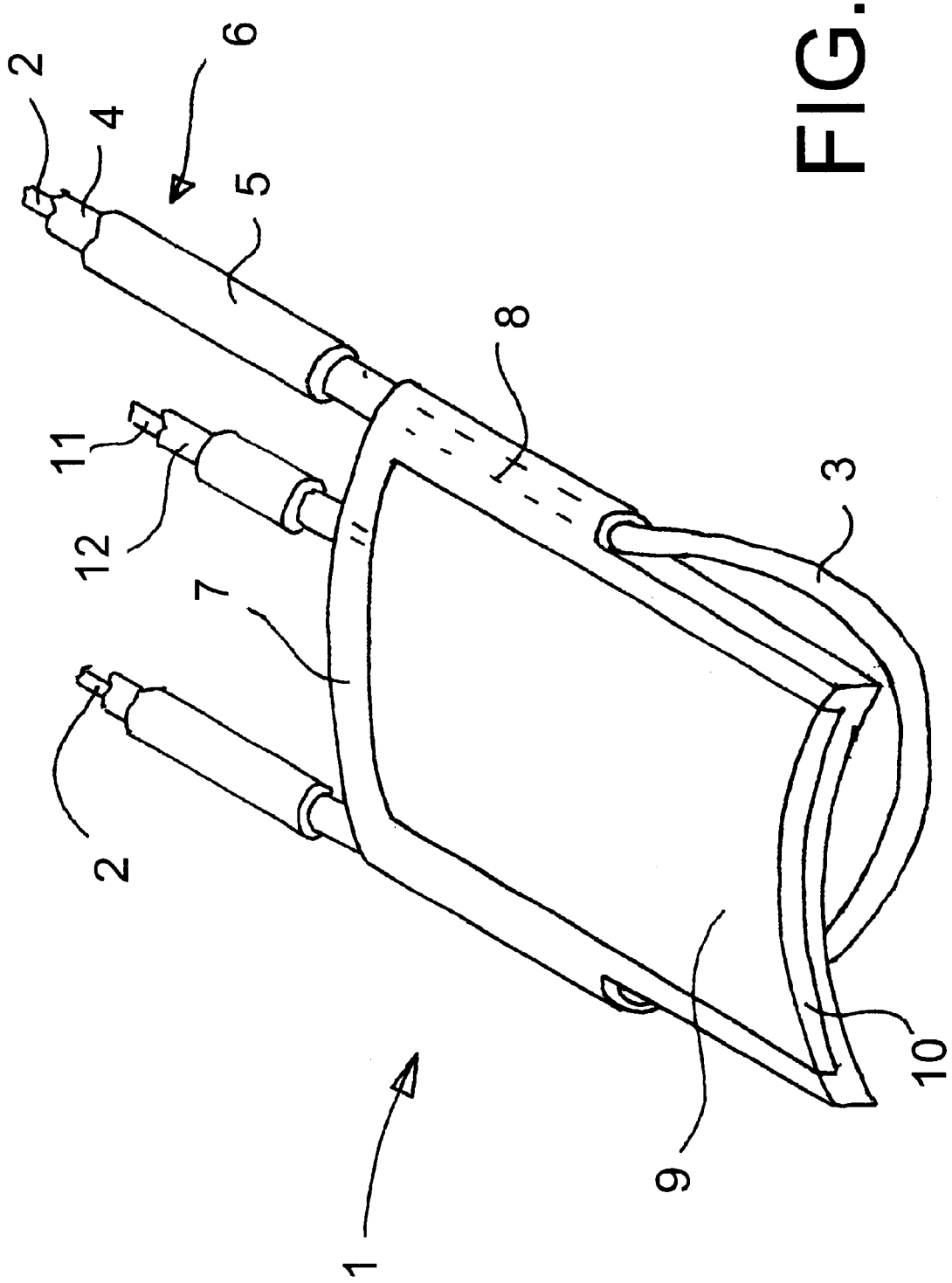
FIG. 1 is a perspective of the distal end zone of an hf resectoscope implement of the invention fitted with an active electrode in the form of a loop.
Figure 5:
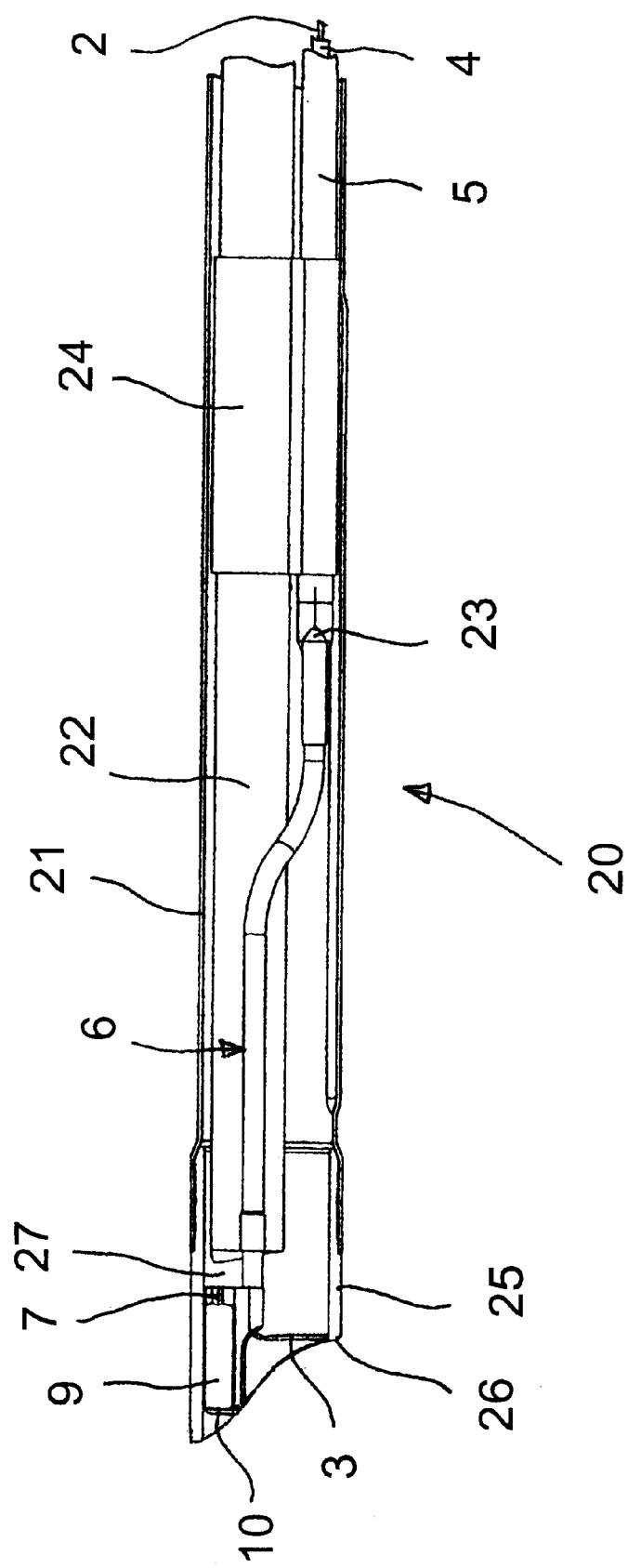
FIG. 5 is a side view of the implement of FIG. 1 in a retracted position.
Figure 6:
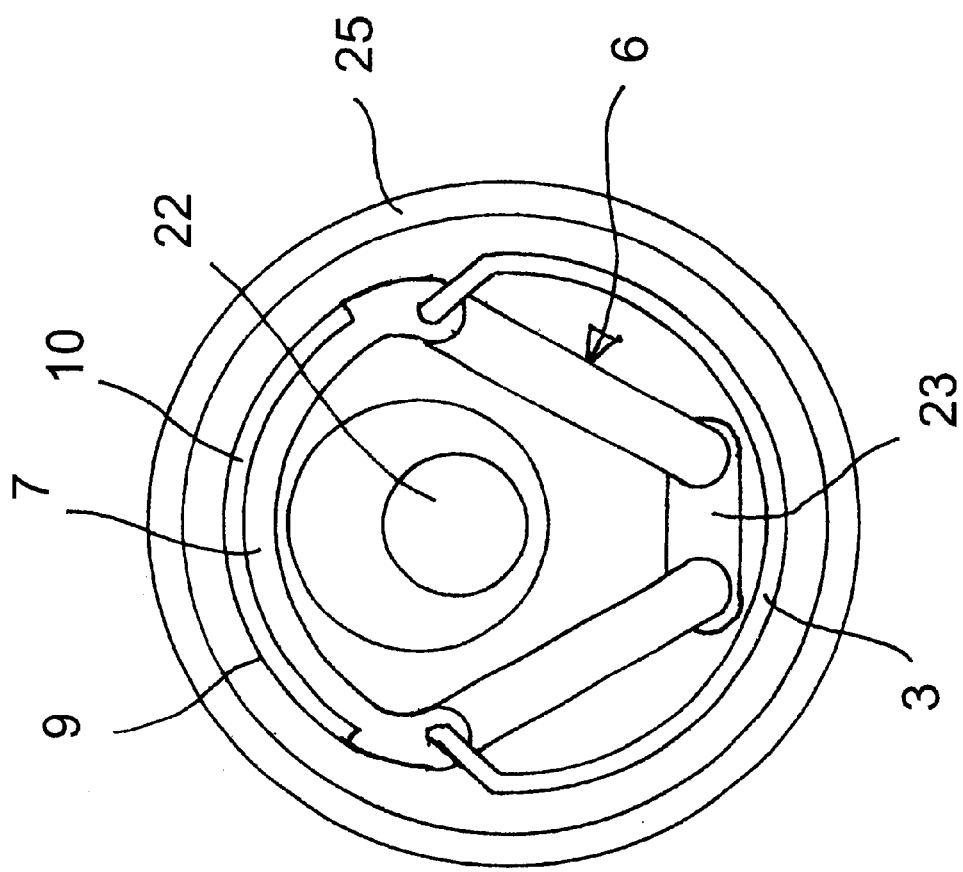
FIG. 6 is a front or end view of the retracted implement shown in FIG. 5.

FIG. 1 shows a distal end zone of an hf resectoscope implement 1 of the invention. The implement 1 is mounted in an exchangeable manner to a resectoscope, as illustrated in FIGS. 4 through 6, and is powered by an hf generator (not shown).

Figure 4:
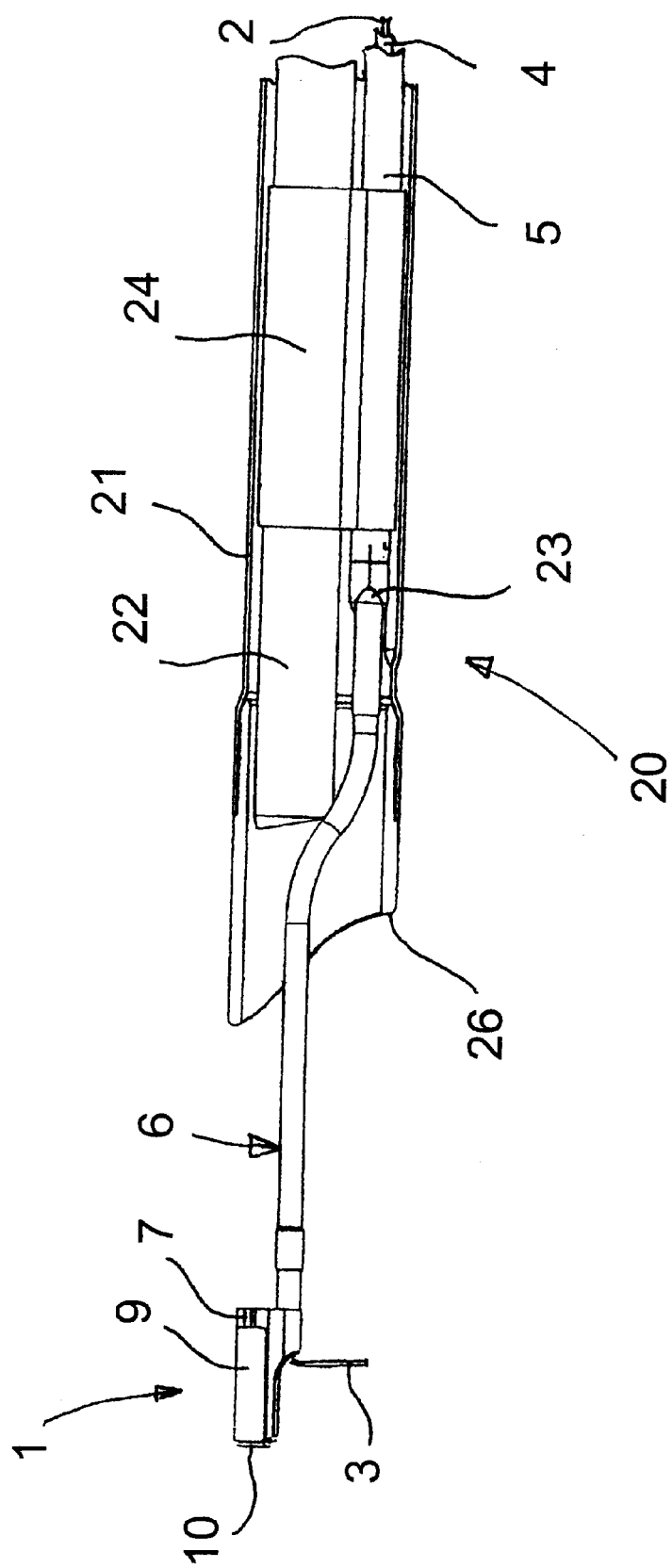
FIG. 4 is a side view of the implement of FIG. 1 in an advanced position out of the stem tube of a resectoscope shown in longitudinal section.

As shown in FIGS. 1 and 4, the implement 1 has an inner conductor 2 passing through the implement's full length and which, except at its proximal contact zone and at its distal zone subtending or defining a cutting loop 3, is clad by an insulator jacket 4. The insulator jacket 4, in turn, runs inside a tube 5 made of a dimensionally stable material. Additionally, the distal zone may be fitted with a ceramic reinforcement to, for instance, increase mechanical strength and electrical safety. At its distal end, the implement 1 bifurcates into two substantially parallel loop support arms 6. FIG. 1, however, only shows the distal segment following the bifurcation.

A topological, cylindrical, convex insulator 7 is mounted between the loop support arms 6 which hold it in place. The insulator 7 has laterally displaced, lengthwise extending boreholes 8 through which the inner conductor 2 runs axially approximately as far as half the length of this insulator 7, the conductor 2 then assuming the shape of a cutting loop 3 constituting the cutting electrode. The plane of the cutting loop 3 is approximately perpendicular to a longitudinal axis of the implement 1. Accordingly, the loop 3 is situated approximately centrally underneath the insulator 7, which receives into its top side a topological neutral electrode 9, for instance a metallic lamella, which is cylindrically curved in the same manner as the insulator 7.

While the insulator 7 shields the neutral electrode 9 at its proximal end, the neutral electrode has an area 10 at its distal end that is bare or free of the insulator 7. The neutral electrode makes contact, by means of a lateral conductor 11 clad by an insulating jacket 12 and advantageously passing through one of the bifurcated tubes while isolated from the inner conductor, with one terminal (pole) of the hf generator (not shown). The cutting loop 3 is connected, via the inner conductor 2, to the hf generator's other terminal.

Figure 2:
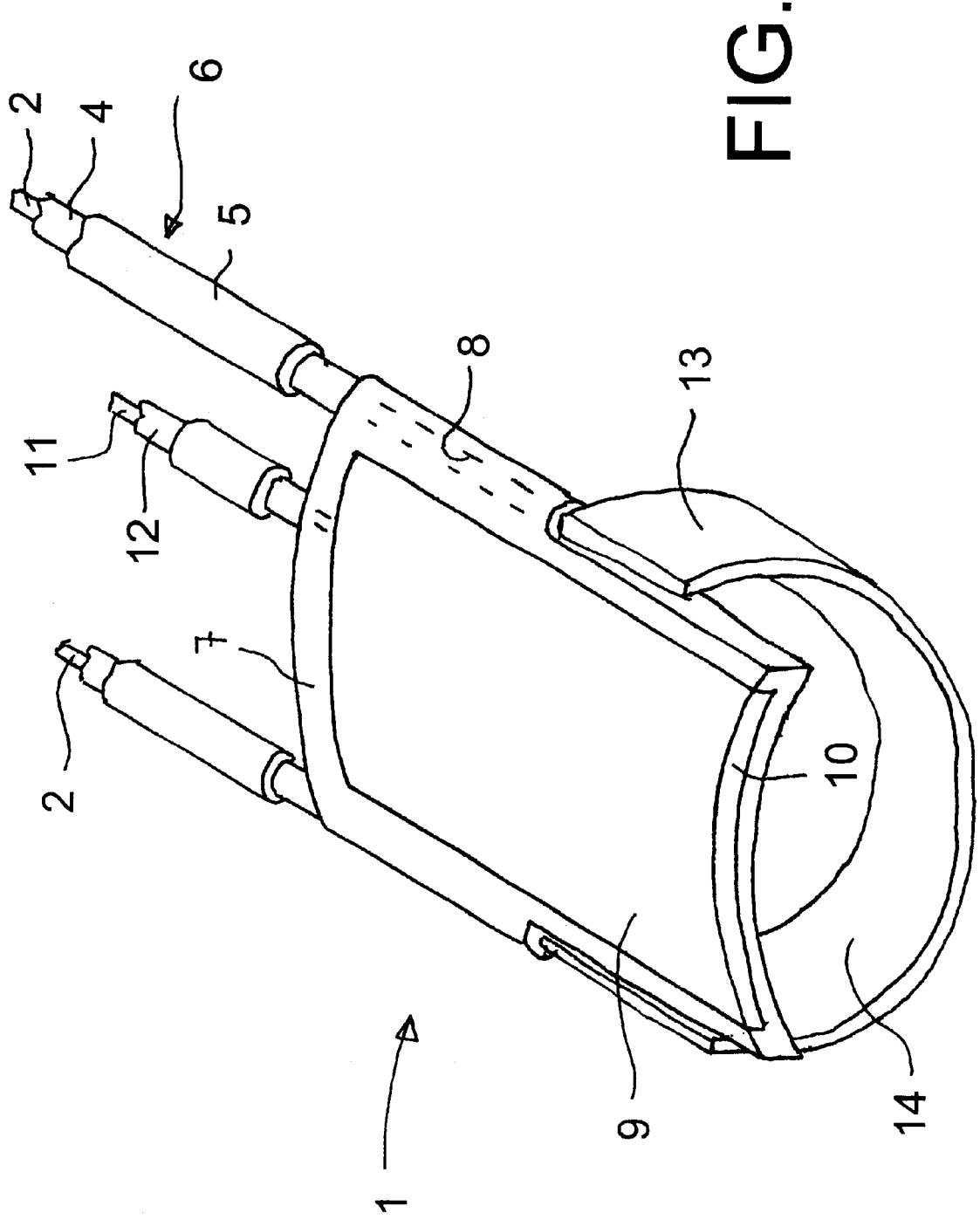
FIG. 2 is a view similar to FIG. 1 of the implement of the invention in an alternative embodiment and fitted with an active electrode in the form of a strip.

FIG. 2 shows an alternative embodiment of the hf implement 1 which substantially corresponds to that of FIG. 1. In this embodiment, the cutting electrode is a lamellar electrode 13 that has an insulating layer 14 fitted on its inside surface. The same references as used in FIG. 1 apply to the otherwise congruent elements.

Figure 3:
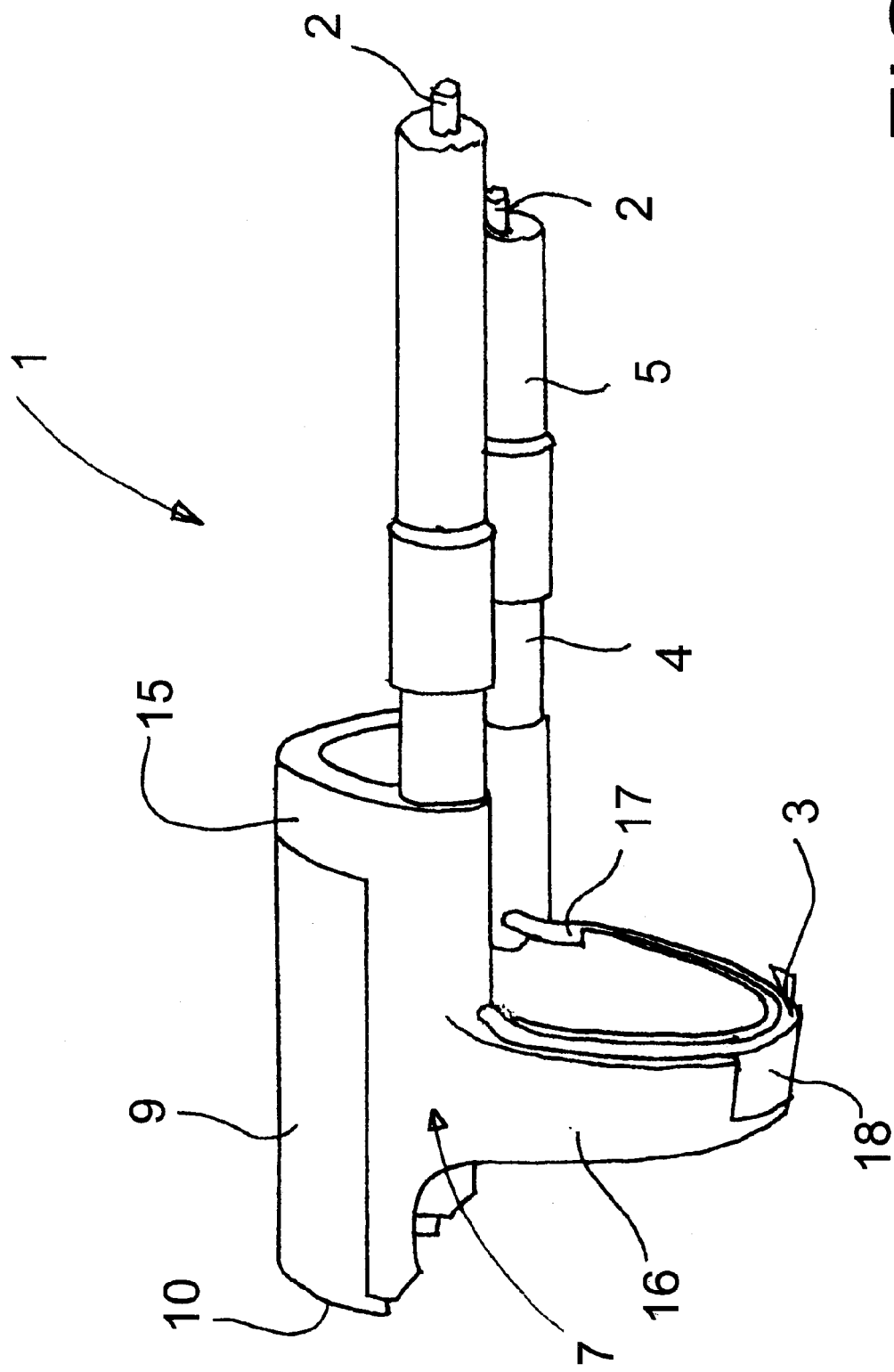
FIG. 3 is a view similar to FIG. 2 showing an alternative insulator and a wire loop of which the lower zone is an active electrode widened into lamella.

An advantageous alternative embodiment of the insulator 7 is shown in FIG. 3. In addition to its cylindrically convex upper or first segment 15, the insulator 7 has an oppositely curved lower or second segment 16. The insulator is one-piece or integrally formed and is, for instance, made of a ceramic. As viewed in axial projection, the insulator 7 substantially subtends a ring. As regards the insulator of FIGS. 1 and 2, FIG. 6 shows that the insulator, together with the cutting loop 3, subtends a ring in axial projection.

The mechanically static behavior of the hf implement 1 is substantially determined by the integral insulator 7 to which is mounted the cutting electrode 3 in wire form at its upper zone 17 and in curved lamellar form 18. In this manner the cutting electrode is made mechanically strong.

Aside from the above-discussed three embodiments of the cutting-electrode, other designs of the state of the art also are applicable, for instance a cutting electrode fitted with flutings or salients. The invention is not restricted to a specific design of the cutting electrode.

When the hf implement 1 is used to cut body tissue in a body cavity filled with an electrically conducting fluid, only the cutting electrode 3 is in electrically conducting contact with the tissue. The current enters the contact site over a small surface, that is at high current density into the tissue to be removed, and in this manner effects its cutting. On the average, this cutting current crosses only a short path through the tissue, whereafter it is diluted over a large cross-section when issuing from the tissue into the electrically conducting fluid on its way to the neutral electrode 9 mounted on the top side of the insulator 7. In addition to this payload current, a stray current without cutting effectiveness passes through the fluid straight between the cutting and the neutral electrodes 3 and 9, this stray current being kept small relative to the payload current because the insulator 7 shields the straight paths between the electrodes 3 and 9, i.e. it constrains a longer path on the current and consequently raises the impedance in the fluid relative to the impedance in the body tissue. The current favoring the path of least impedance, the geometry of the insulator 7 causes increased current through the body tissue, i.e. a reduction in the stray current.

FIG. 3 shows that the lower or second segment 16 of the insulator 7 shields the wire-like or filamentary zone 17 of the cutting loop 3 relative to the proximal side and the lamellar zone 18 of the cutting loop 3 relative to the top side.

FIG. 4 shows an implement 1 of the invention of the embodiment of FIG. 1 in its advanced mode integrated into a commercial resectoscope 20, the implement being advanced and retracted axially by means of an omitted resectoscope actuator connected to the implement 1. The forward motion in the distal direction also is termed "advance" and the rearward motion in the proximal direction also is called "retraction". The resectoscope 20 consists of the hf implement 1 and a stem tube 21 receiving the optics 22, which in this instance is shown mounted eccentrically and which may be proximally followed for instance by an ocular or picture recording device. Furthermore, the resectoscope 20 is designed such that the rinsing fluid can continuously issue from the stem tube 21 and also be evacuated again. For instance, the stem may be a double stem fitted with back-flow entry apertures in its outer wall. The related inflow and outflow adapters are situated in the resectoscope's proximal region, which is not shown in further detail.

A guide bush 24 is affixed proximally from the bifurcation site 23 to the tube 5 of the implement 1 and, once installed, will enclose the optics with slight play and be able to glide on it, as a result of which the implement 1, when being axially displaced relative to the optics, is supported in a stabilized manner. In the assembled state, the bifurcation site 23 is configured below the optics. However, the two loop supports 6 run distally from the bifurcation site 23 obliquely upward in order to run laterally past the optics 22.

This configuration is further elucidated in FIG. 5, which shows the hf implement 1 in the retracted position, and also in the related front view of FIG. 6. The loop support arms 6 run laterally past the optics 22. The dimensions of the implement 1 are selected such that it can be wholly retracted into the resectoscope. In other words, the distal end zone of the hf implement 1 is wholly covered in cross-sectional side view by the stem zone of the resectoscope 20, the stem zone being shown as an insulated beak-shaped tip 25. It will be noted that the cutting loop 3 can be retracted at least to the level of the cutting edge 26 in order to cut off a strip of body tissue in the course of a retraction. When the cutting loop 3 moves past the cutting edge 26 during the retraction, the end of the body tissue will be cut off between the cutting loop 3 and the cutting edge 26 as if between scissors. A gap 27 remains clear between the neutral electrode 9 and the optics 22. The neutral electrode is covered by the resectoscope tip 25, except for the zone 10 left uncovered distally from the insulator 7.

FIG. 6 is a front view and shows a cross-sectionally circular tip 25 of the resectoscope 20. Laterally and above the optics 22, which conventionally is mounted eccentrically above the center axis and which, for instance, is a 12° optics, the loop support arms 6 support the cutting loop 3 which is substantially semi-circular and runs in arcuate downward manner a distance from the wall of the tip 25. The insulator 7 abuts the loop support arms 6 and runs arcuately above the optics. This Figure shows that an approximately circular residual and clear space remains between the downward arcuate cutting loop 3 and the upward arcuate insulator 7 or the neutral electrode 9 mounted thereto, and the surgeon uses the optics 22 mounted in the free space/window to freely survey the field of surgery. Moreover, neither the cutting electrode 3, the neutral electrode 9, nor the insulator 7 hamper any illuminating light applied through the optics.

The drawings only show bifurcated embodiments. However, single conductor electrodes are included in the invention as well. Similar considerations apply to the optics which herein is shown always mounted eccentrically above the cross-sectional center of the stem. However, the optics clearly may also be mounted centrally or below the cross-sectional stem center without transcending thereby the scope of the present invention.

What is claimed is:

1. A high-frequency (hf) resectoscope implement (1) for cutting body tissue in a body cavity filled with an electrically conducting fluid, comprising a loop support (6) and a loop-shaped cutting electrode (3) mounted distally to said loop support, a plane of said loop-shaped cutting electrode slanting relative to a longitudinal axis of the loop support (6), said implement further comprising a neutral electrode (9) mounted on said support, wherein an insulator (7) is mounted between the cutting and neutral electrodes (3, 9) at the loop support (6) such that any straight geometric line drawn between the electrodes (3, 9) passes through the insulator (7), and wherein the neutral electrode (9) and the insulator (7) are configured such that, when disposed in an active position within a resectoscope (20), they do not significantly hamper a view through an optics (22), which is mounted in a stem tube (21) of said resectoscope (20).

2. The implement (1) as claimed in claim 1, wherein the neutral electrode (9) is mounted distally on the loop support (6).

3. The implement (1) as claimed in claim 1, wherein the neutral electrode (9) is mounted on a side of the insulator (7) that faces away from the cutting electrode (3).

4. The implement (1) as claimed in claim 3, wherein the neutral electrode (9) is mounted surface-on-surface on the insulator (7).

5. The implement (1) as claimed in claim 3, wherein the neutral electrode (9) is embedded in the insulator (7).

6. The implement (1) as claimed in claim 5, wherein the neutral electrode (9) comprises a distal zone (10) that is not covered by the insulator (7).

7. The implement (1) as claimed in claim 1, wherein a curvature of the insulator (7) is inverted relative to a curvature of the cutting electrode (3).

8. The implement (1) as claimed in claim 1, wherein the loop support (6) is bifurcated into two parallel bars, the cutting electrode (3) being configured in substantially semi-circular shape between said bars and transversely to an axis of said bars, and wherein the insulator (7) adjoins both bars.

9. The implement (1) as claimed in claim 7, wherein an axial projection of the cutting electrode (3), together with that of the curved insulator (7) with the neutral electrode (9) mounted on it, substantially subtend a circle.

10. The implement (1) as claimed in claim 9, wherein the insulator (7) is integral and consists of a first segment (15) exhibiting a curvature that is inverted relative to a curvature of the cutting electrode (3) and a second segment (16) distally hugging a topology of the cutting electrode (3).

11. The implement (1) as claimed in claim 10, wherein the cutting electrode (3) is affixed to the second segment (16) of the insulator (7).

12. The implement (1) as claimed in claim 11, wherein a lower zone of the cutting electrode (3) is designed as a wire (17) widened into a lamella (18), said lamella (18) being mounted on an outside surface of the second segment (16) of the insulator (7).

* * * * *